United States Patent [19]
Odagiri et al.

[11] Patent Number: 5,749,366
[45] Date of Patent: May 12, 1998

[54] MOTION COMPENSATING PULSE RATE MONITOR WITH MOTION SENSOR AND LEVEL DISCRIMINATOR

[75] Inventors: Hiroyuki Odagiri, Chiba; Naoaki Yasukawa, Suwa, both of Japan

[73] Assignees: Seiko Instruments Inc.; Seiko Epson Corporation, both of Japan

[21] Appl. No.: 620,930

[22] Filed: Mar. 22, 1996

[30] Foreign Application Priority Data

Mar. 23, 1995 [JP] Japan .................. 7-064405
Feb. 23, 1996 [JP] Japan .................. 8-036815

[51] Int. Cl.$^6$ .................................................. A61B 5/024
[52] U.S. Cl. ........................ 128/690; 128/687; 128/689
[58] Field of Search ............................... 128/687, 689, 128/690, 696, 700, 714

[56] References Cited

U.S. PATENT DOCUMENTS

| | | | |
|---|---|---|---|
| 4,305,401 | 12/1981 | Reissmueller et al. | 128/690 |
| 4,338,950 | 7/1982 | Barlow Jr., et al. | 128/687 |
| 4,807,639 | 2/1989 | Shimizu et al. | 128/690 |
| 5,197,489 | 3/1993 | Conlan | 128/690 |
| 5,263,491 | 11/1993 | Thornton | 128/700 |
| 5,280,791 | 1/1994 | Lavie | 128/696 |
| 5,515,858 | 5/1996 | Myllymäki | 128/690 |
| 5,524,637 | 6/1996 | Erickson | 128/779 |
| 5,539,706 | 7/1996 | Takenaka et al. | 128/690 |

FOREIGN PATENT DOCUMENTS

| | | |
|---|---|---|
| 614070 | 9/1994 | European Pat. Off. . |
| 638281 | 2/1995 | European Pat. Off. . |
| 653182 | 5/1995 | European Pat. Off. . |
| 659384 | 6/1995 | European Pat. Off. . |
| 2700683 | 7/1994 | France ............... A61B 5/024 |
| 94 03102 | 2/1994 | WIPO . |

*Primary Examiner*—William E. Kamm
*Assistant Examiner*—Carl H. Layno
*Attorney, Agent, or Firm*—Adams & Wilks

[57] ABSTRACT

A pulse rate monitor allows a user's pulse rate to be measured and displayed continuously while removing the inaccuracies caused by motion of the user, by detecting the motion level and determining whether an accurate pulse rate measurement can be taken based upon the detected motion. The most recent accurate pulse rate measurement is stored in memory and the pulse rate is estimated when a user is undergoing too much movement for obtaining accurate measurements by using the stored pulse rate and the magnitude of the detected movement.

17 Claims, 13 Drawing Sheets

QUIET STATE

ELECTRO-CARDIOGRAM (70 PULSES/MIN.)

PULSE WAVEFORM

RECTANGULAR MODULATED WAVEFORM (70 PULSES/MIN.)

MOTION STATE (STROKE PITCH = 100 STROKES/MIN.)

ELECTRO-CARDIOGRAM (120 PULSES/MIN.)

PULSE WAVEFORM

RECTANGULAR MODULATED WAVEFORM (98 PULSES/MIN.)

TO A/D CONVERTER

TO PULSE SIGNAL
AMPLIFYING
CIRCUIT

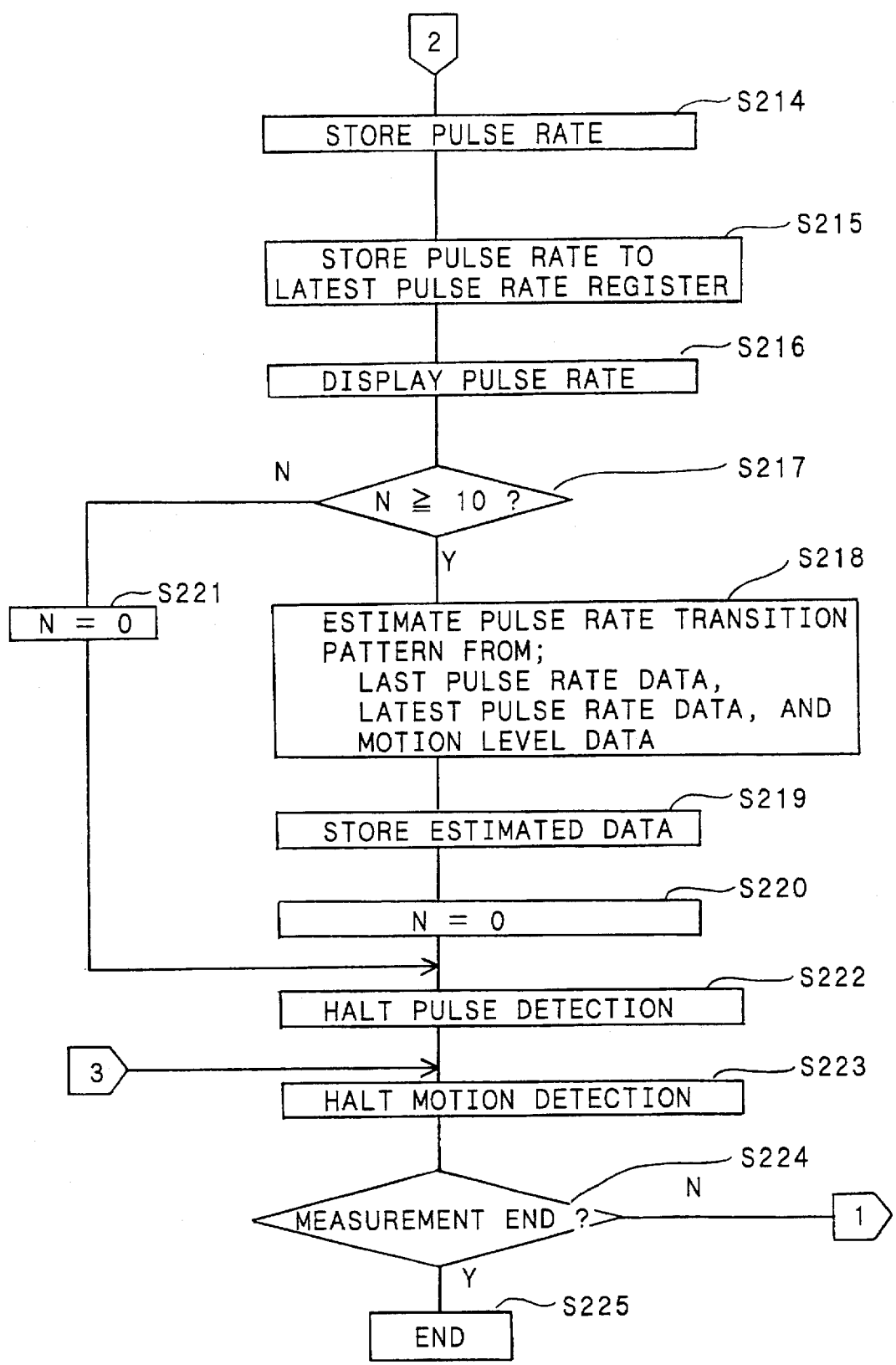

MOTION COMPENSATING PULSE RATE MONITOR WITH MOTION SENSOR AND LEVEL DISCRIMINATOR

BACKGROUND OF THE INVENTION

The present invention relates generally to a pulse rate monitor for continuously measuring a pulse rate and, more particularly, to a pulse rate monitor which allows a pulse rate to be measured and recorded continuously for a long period of time while removing a disturbance of a measured value of the pulse rate caused by motion.

The number of people to attempt to maintain their health by playing sports and engaging in activities such as walking and jogging is increasing. Further, the number of people who monitor their pulse as an index of their health is also increasing, and a pulse rate monitor is widely used among those people in such circumstances.

FIG. 3 is a functional block diagram showing an operation of a prior art pulse rate monitor. Pulse detecting means 301 detects a pulse signal and outputs the detected pulse signal to a pulse amplifying means 302. The pulse amplifying means 302 amplifies and shapes the waveform of the pulse signal and outputs it to a pulse rate calculating means 304. The pulse rate calculating means 304 converts the periodic signal of the pulse from the pulse amplifying means 302 into a pulse rate based on a reference timing signal supplied by time counting means 303.

Displaying means 305 displays the pulse rate calculated by the pulse rate calculating means 304 as well as the timing data counted by the time counting means 303. Inputting means 306 is a switch manipulated when measuring a pulse rate and its output is connected to pulse detection controlling means 307. The pulse detection controlling means 307 controls the activation and inactivation of the pulse detecting means 301, the pulse amplifying means 302 and the pulse rate calculating means 304 based on the input from the inputting means 306.

When a user desires to measure their own pulse using the prior art pulse rate monitor, however, it is necessary to manipulate the switch to activate the pulse detecting function and to measure the pulse consciously by interrupting an exercise in the middle thereof. The reason why the conventional device can measure only the short term pulse rate is because it is extremely difficult to take a pulse during a motion.

FIG. 4 shows a pulse waveform taken at the finger tip at the same time with an electrocardiogram in a rest state. A clear pulse waveform which is behind the electrocardiogram more or less can be obtained in the rest state. The same number of rectangular waveforms, modulated from the pulse waveforms, with that of the electrocardiogram are also generated. In the figure, the rectangular waveforms of 70 pulses/min. are generated corresponding to the same number of the electrocardiogram of 70 pulses/min.

FIG. 5 shows an electrocardiogram and a pulse waveform obtained during a motion state in which the arms are swung at a stroke pitch of 100 strokes/min. Because the electrocardiogram is measured by pasting an electrode on the chest, it is possible to obtain a stable waveform even during the motion state. In contrary, the pulse waveform is disturbed and the number of rectangular modulated waveforms is not matched with that of the electrocardiogram. In the example of the figure, the number of rectangular waveform is 98 pulses/min., though the number of electrocardiogram is 120 pulses/min.

The reason why this happens may be that while changes in the quantity of blood in a blood vessel are monitored in the measurement of pulse, differing from the electrocardiogram, the flow of blood itself is changed within the blood vessels by motion. Because the flow of blood itself which is an object to be measured thus changes, it is very difficult to measure pulse during a motion. Accordingly, the conventional pulse rate monitors have been constructed supposing that a pulse is measured only in a rest state.

However, considering the fact that vital data such as pulse rate is meaningful, originally, only when a large number of such data is sampled, the conventional pulse rate monitors can not be said to be truly useful.

SUMMARY OF THE INVENTION

It is an object of the present invention to provide a pulse rate monitor which allows a pulse rate to be measured unconsciously and continuously.

It is another object of the present invention to provide a pulse rate monitor which allows a health condition or mental state of a user to be judged from a transition pattern of a measured pulse rate.

It is a further object of the present invention to provide a pulse rate monitor which is provided with a function of estimating pulse rate data of a period during which it has been impossible to measure a pulse.

In order to achieve the aforementioned objects, the present invention comprises motion detecting means for detecting a motion by a motion sensor and outputting an analog voltage signal; A/D converting means for converting the output signal of the motion detecting means into a digital signal; motion level discriminating means for discriminating whether it is possible to measure a pulse based on the digital signal output from the A/D converting means and outputting a control signal corresponding to a result of the discrimination; pulse rate measurement means comprising pulse rate detecting means for detecting a pulse from a body and outputting a living periodic signal according to the detected pulse, and pulse rate calculating means for converting the periodic signal of the pulse output from the pulse detecting means into pulse rate data; pulse rate storing means for selectively holding the pulse rate data output from the pulse rate calculating means by the control signal output from the motion level discriminating means; displaying means for displaying the pulse rate data output from the pulse rate storing means; and timing signal generating means for outputting a predetermined timing signal to the pulse rate calculating means and displaying means.

The present invention further comprises, in addition to the structure described above, time counting means for counting time data of the current time; pulse detection controlling means for controlling activation and inactivation of the pulse detecting means and the pulse rate calculating means based on the control signal from the motion level discriminating means; pulse rate storage controlling means for causing the pulse data output from the pulse rate calculating means and the time data of the time counting means to be stored in the pulse rate storing means when the output of the pulse detection controlling means permits the detection of a pulse; read out controlling means for controlling an address for reading contents stored in the pulse rate storing means; inputting means for controlling the read out controlling means with an arbitrary timing; displaying means for displaying the data of the pulse rate storing means and the time data of the time counting means; acceleration detection and A/D conversion controlling means for activating the motion detecting means and the A/D converting means intermittently at predetermined intervals; timing signal generating means for outputting a predetermined timing signal to the acceleration detection and A/D conversion controlling means, pulse rate calculating means, time counting means and displaying means.

The present invention may further comprise pattern storing means for storing a reference transition pattern of a predetermined pulse rate; pattern comparing means for comparing an actually measured transition pattern of a pulse rate stored in the pulse rate storing means with the reference transition pattern stored in the pattern storing means; and comparison result discriminating means for discriminating characteristics of the actually measured pulse rate transition pattern from a result of comparison of the pattern comparing means.

Or, the present invention may be added with motion level storing means for storing an output signal of A/D converting means when an output of the motion level discriminating means indicates that it is impossible to measure a pulse; and pulse rate estimating means for estimating a pulse rate during the pulse unmeasurable period based on the motion level data stored in the motion level storing means and the pulse rate data stored in the pulse rate storing means.

As described above, according to the pulse rate monitor of the present invention, it becomes possible to obtain continuous pulse data in a span of half day or one day, though it may be interruptive, by monitoring a motion level, e.g., a motion of arms, periodically by the motion detecting means and by measuring pulse when the motion is relatively small and it is possible to measure a pulse. Further, it becomes possible to obtain data related to a motion state by estimating a pulse rate during when the motion of the arms is large and no pulse can be measured from the motion level which corresponds to the motion of the arms.

While it has been said that a biological information such as a pulse rate is meaningless if it is the information taken in a short term, the present invention has an advantage that it can provide the truly useful pulse rate monitor which allows to record pulse rate data continuously while being unconscious.

BRIEF DESCRIPTION OF THE DRAWINGS

FIG. 14 is a chart showing one part of another flow of an operation in measuring a pulse.

DETAILED DESCRIPTION OF THE PREFERRED EMBODIMENTS

Several embodiments of the present invention will hereinafter be described with the reference to the drawings.

First, some functional embodiments according to the basic concept of the present invention will be explained by a combination of functional means. Several detailed embodiments will be explained later.

Figure 1:
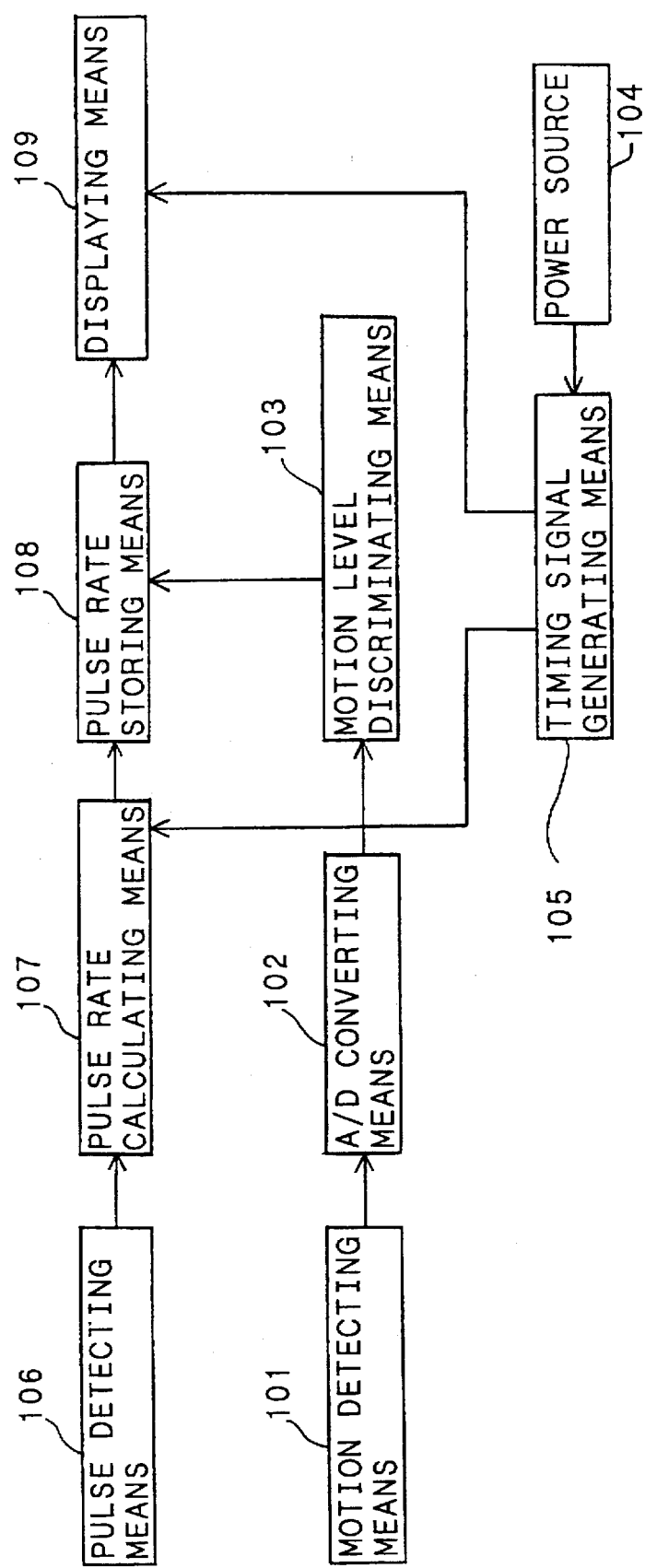
FIG. 1 is functional block diagram showing a basic structure of the present invention.

FIG. 1 is a functional block diagram showing a basic structure of the present invention which detects a motion level while detecting a pulse and stores and displays only the correct pulse by discriminating whether the motion level is within a predetermined range or not.

Motion detecting means 101 outputs an analog output voltage signal which is proportional to the motion of a user's arms to A/D converting means 102. The A/D converting means 102 converts the analog signal input from the motion detecting means 101 into a digital signal and outputs it to motion level discriminating means 103. Timing signal generating means 105 which is operated by a power source 104 outputs a predetermined timing signal to pulse rate calculating means 107 and displaying means 109. Pulse detecting means 106 detects a pulse and outputs its periodic signal to the pulse rate calculating means 107. Based on the timing signal from the timing signal generating means 105, the pulse rate calculating means 107 converts the periodic signal input from the pulse detecting means 106 into a pulse rate, i.e., a number of pulses per minute, and outputs it to pulse rate storing means 108.

The motion level discriminating means 103 discriminates whether it is possible to detect a pulse or not from the level of the digital signal proportional to the motion input from the A/D converting means 102 and when it is possible to detect the pulse, outputs a hold signal for holding the pulse rate data to the pulse rate storing means 108. The pulse rate storing means 108 holds the output of the pulse rate calculating means 107 in response to the hold signal from the motion level discriminating means 103 and outputs the held data to the displaying means 109. The displaying means 109 displays the data held in the pulse rate storing means 108 in accordance with the timing signal input from the timing signal generating means 105.

Thus, the pulse rate data held in the pulse rate storing means 108 is updated only when there is a hold signal output from the motion level discriminating means 103. Accordingly, the latest pulse rate data in the state in which the motion level is low and the pulse can be reliably counted is always displayed on the displaying means 109.

Figure 2:
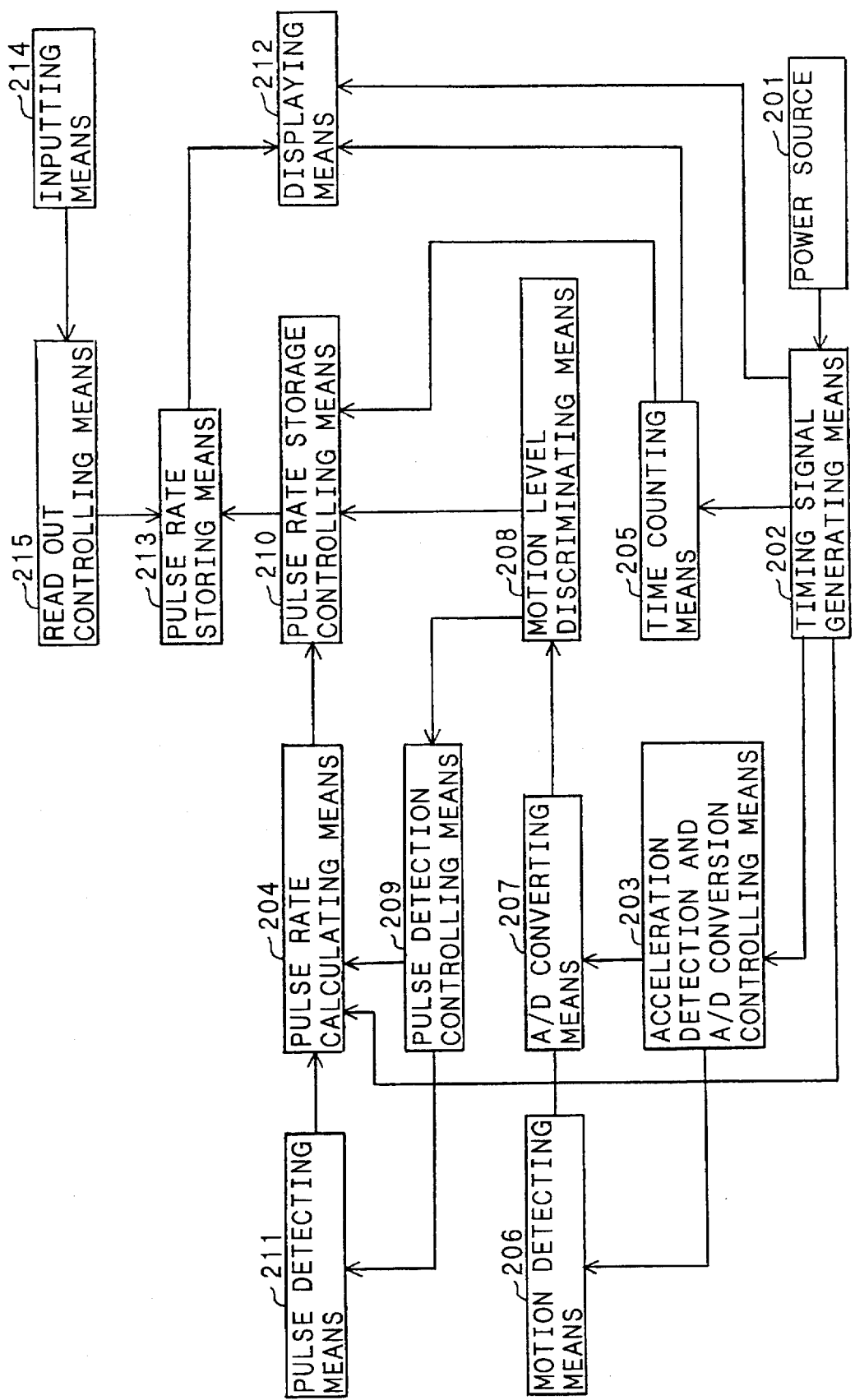
FIG. 2 is a functional block diagram showing one example of a structure of the present invention.
Figure 3:
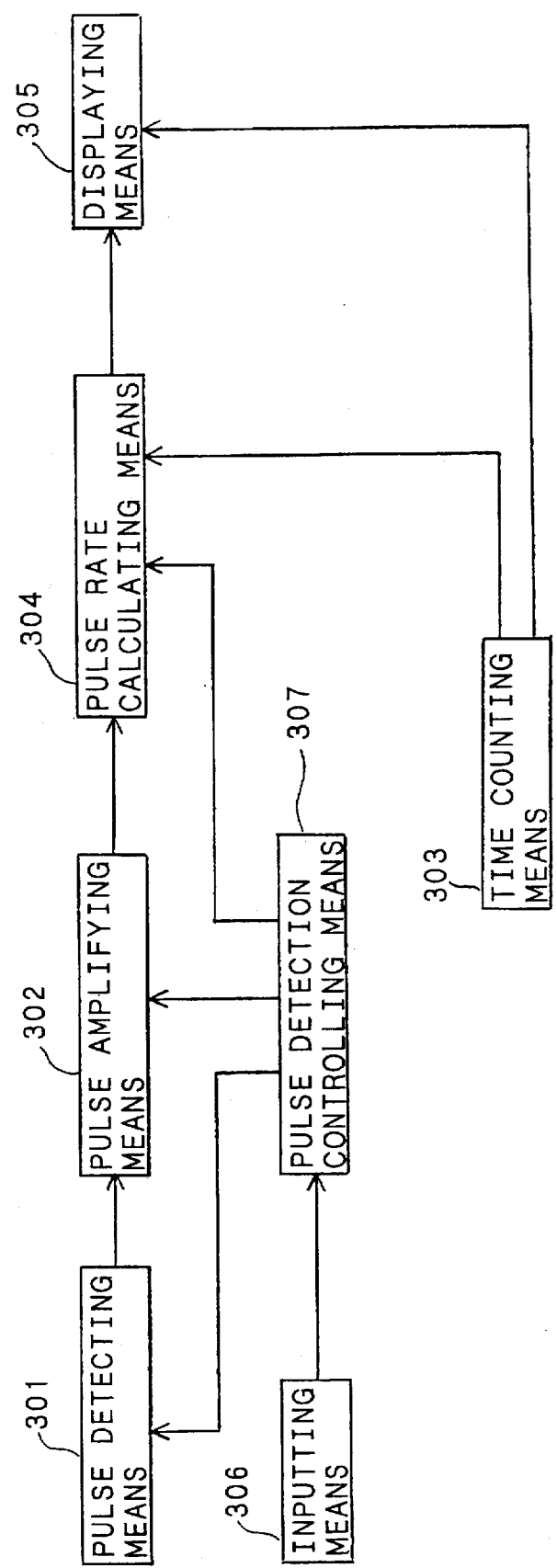
FIG. 3 is a functional block diagram of a prior art pulse rate monitor.
Figure 4:
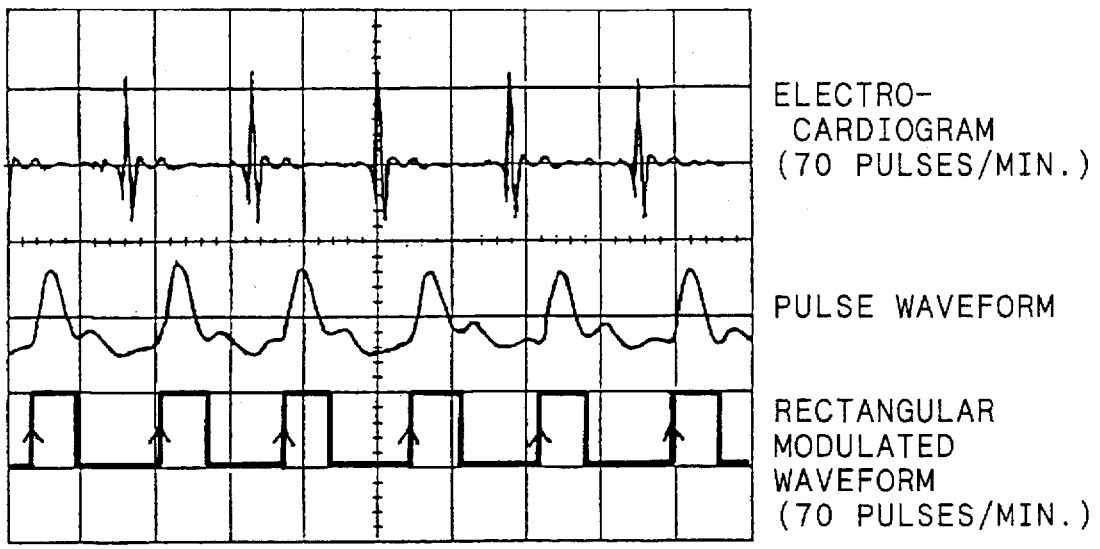
FIG. 4 is a diagram showing an electrocardiogram and a pulse waveform in a quiet state.
Figure 5:
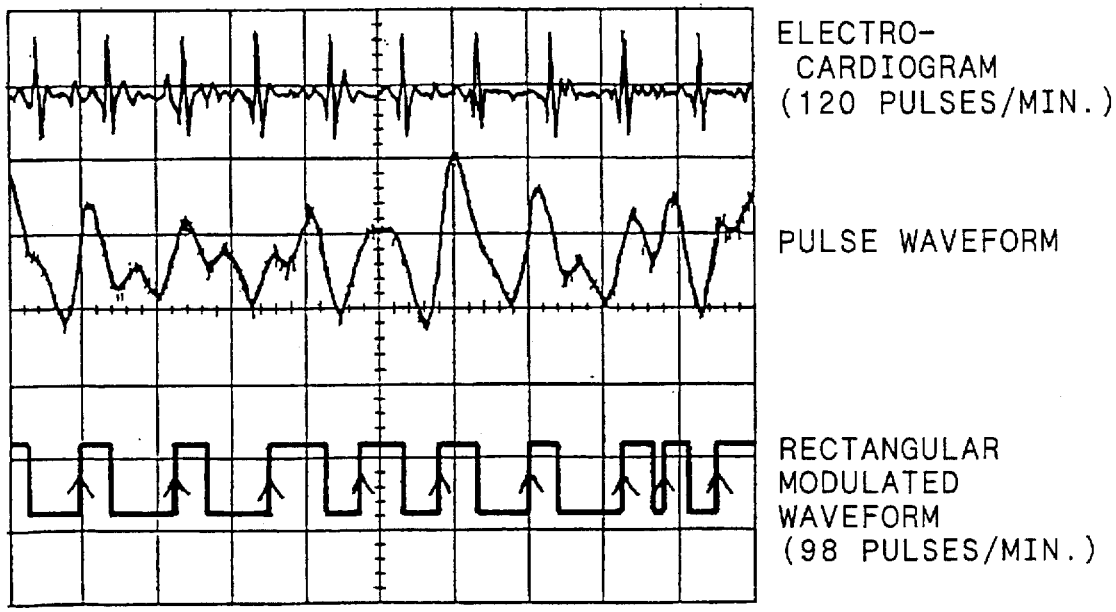
FIG. 5 is a diagram showing an electrocardiogram and a pulse waveform in a motion state.

FIG. 2 is a block diagram in which the functions of actuating the detection of motion intermittently at predetermined intervals and of counting the current time are added to the basic structure of the present invention shown in FIG. 1 to reduce a power consumption and to allow a transition of pulse rate to be confirmed by storing the time when the pulse rate is detected in storing the pulse rate.

Timing signal generating means 202 operated by a power source 201 outputs a predetermined timing signal to pulse rate calculating means 204, acceleration detection and A/D conversion controlling means 203, time counting means 205 and displaying means 212, respectively.

The acceleration detection and A/D conversion controlling means 203 activates motion detecting means 206 and A/D converting means 207 intermittently based on the timing signal from the timing signal generating means 202. The motion detecting means 206 outputs an analog voltage signal proportional to the motion of the user's arms to the A/D converting means 207. The A/D converting means 207 converts the analog voltage signal output by the motion detecting means 206 into a digital signal and outputs it to motion level discriminating means 208. Based on the level of the digital signal output from the A/D converting means 207, the motion level discriminating means 208 discriminates whether it is possible to detect a pulse or not and outputs a control signal to pulse detection controlling means 209 and pulse rate storage controlling means 210.

Based on the control signal output by the motion level discriminating means 208, the pulse detection controlling means 209 activates pulse detecting means 211 and the pulse rate calculating means 204 when it is possible to detect a pulse. The pulse detecting means 211 detects the pulse and outputs its periodic signal to the pulse rate calculating means 204. The pulse rate calculating means 204 converts the periodic signal of the pulse input from the pulse detecting means 211 into pulse rate data per one minute based on the timing signal from the timing signal generating means 202 and outputs it to the pulse rate storage controlling means 210.

The time counting means 205 counts time based on the timing signal from the timing signal generating means 202 and outputs time data to the pulse rate storage controlling means 210 and the displaying means 212. When the control signal output from the motion level discriminating means 208 indicates that it is possible to measure a pulse, the pulse rate storage controlling means 210 outputs the pulse rate data output from the pulse rate calculating means 204 and the time data output from the time counting means 205 to pulse rate storing means 213. The pulse rate storing means 213 stores the pulse rate data and time data transmitted from the pulse rate storage controlling means 210 and outputs the latest pulse data and time data to the displaying means 212.

Read out controlling means 215 controlled by inputting means 214 controls which of the plurality of pulse data and time data stored in the pulse rate storing means 213 should be read.

Among the functional blocks in FIG. 2, the motion detecting means 206 and the A/D converting means 207 operate intermittently and the motion level discriminating means 208 discriminates whether it is possible to detect a pulse. When it is possible to detect a pulse, the pulse detecting means 211 and the pulse rate calculating means 204 are activated to obtain pulse data. The obtained pulse data and the time thereof are then stored in the pulse rate storing means 213. As a result, the latest pulse data is always displayed on the displaying means and in the same time, a saving of power consumption can be realized by activating the pulse detecting means 211 and the motion detecting means 206 intermittently. Further, it becomes possible to confirm a transition of pulse rate and to display any past pulse data on the displaying means 212 by the inputting means 214.

Figure 7:
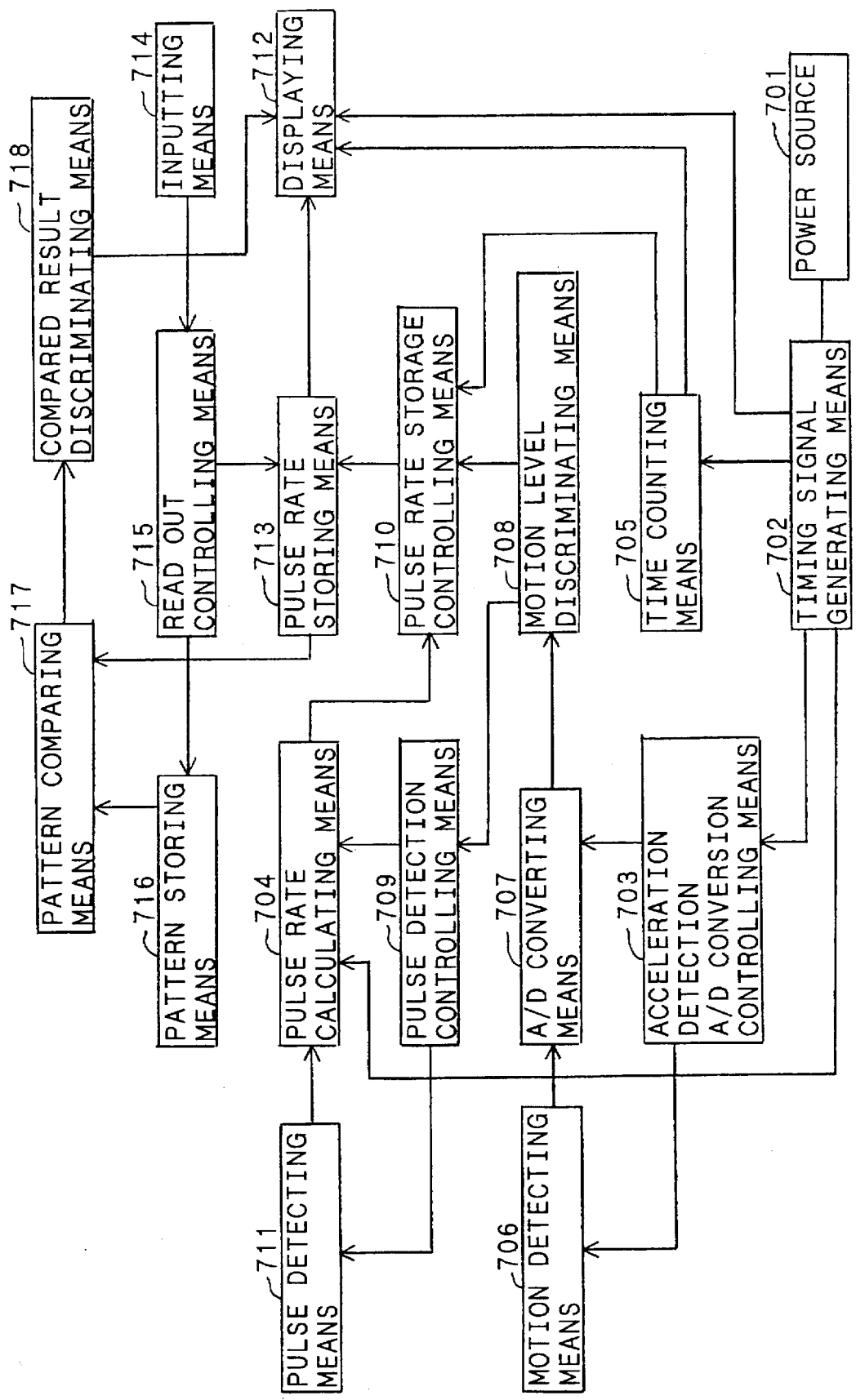
FIG. 7 is a functional block diagram showing other example of the structure of the present invention.

FIG. 7 is a block diagram wherein a function of storing a reference transition pattern of pulse rate in advance is provided to the basic structure of the present invention shown in FIG. 1, beside the functions of activating the motion detection intermittently at predetermined intervals and of counting the current time, to discriminate a health condition or mental state of the user by comparing an actually measured pulse rate transition pattern and the reference transition pattern stored in advance.

Among the functional blocks in the figure, those having the same function with those shown in FIG. 2 are designated with the same block number, with respect to their two lower digits, and explanation thereof will be partly omitted. Here, functional blocks added anew in FIG. 7 will be mainly explained.

Several kinds of reference transition patterns of typical pulse rates are stored in pattern storing means 716. It is also possible to write and store reference pulse rate transition patterns intrinsic to the user in the pattern storing means 716 as necessary. The pattern storing means 716 outputs time data and the pulse rate data at an address specified by read out controlling means 715 to pattern comparing means 717. The pattern comparing means 717 compares the data output from pulse rate storing means 713 with the data output from the pattern storing means 716 and outputs a result of the comparison to comparison result discriminating means 718. The comparison result discriminating means 718 outputs a result of the discrimination to displaying means 712.

According to the functional blocks in FIG. 7, the reference pulse rate transition pattern stored in the pattern storing means 716 and the transition pattern of the measured pulse rate stored in the pulse rate storing means 713 are compared, the result of the comparison is discriminated and the result of the discrimination is displayed on the displaying means 712.

Because a transition pattern of a pulse rate taken when a motion level is relatively low and a pulse can be taken continuously is the object of the comparison, it is preferable to take transition patterns during sleep or a light exercise such as walking for example as the transition patterns to be stored in the pattern storing means 716. It then becomes possible to discriminate a quality of sleep by storing the transition pattern of a typical pulse rate during sleep in the pattern storing means 716 in advance. Further, it becomes possible to discriminate and evaluate a stability of mental state from a fluctuation of the pulse rate transition pattern by storing a pulse rate transition pattern in a quiet state in advance.

Figure 8:
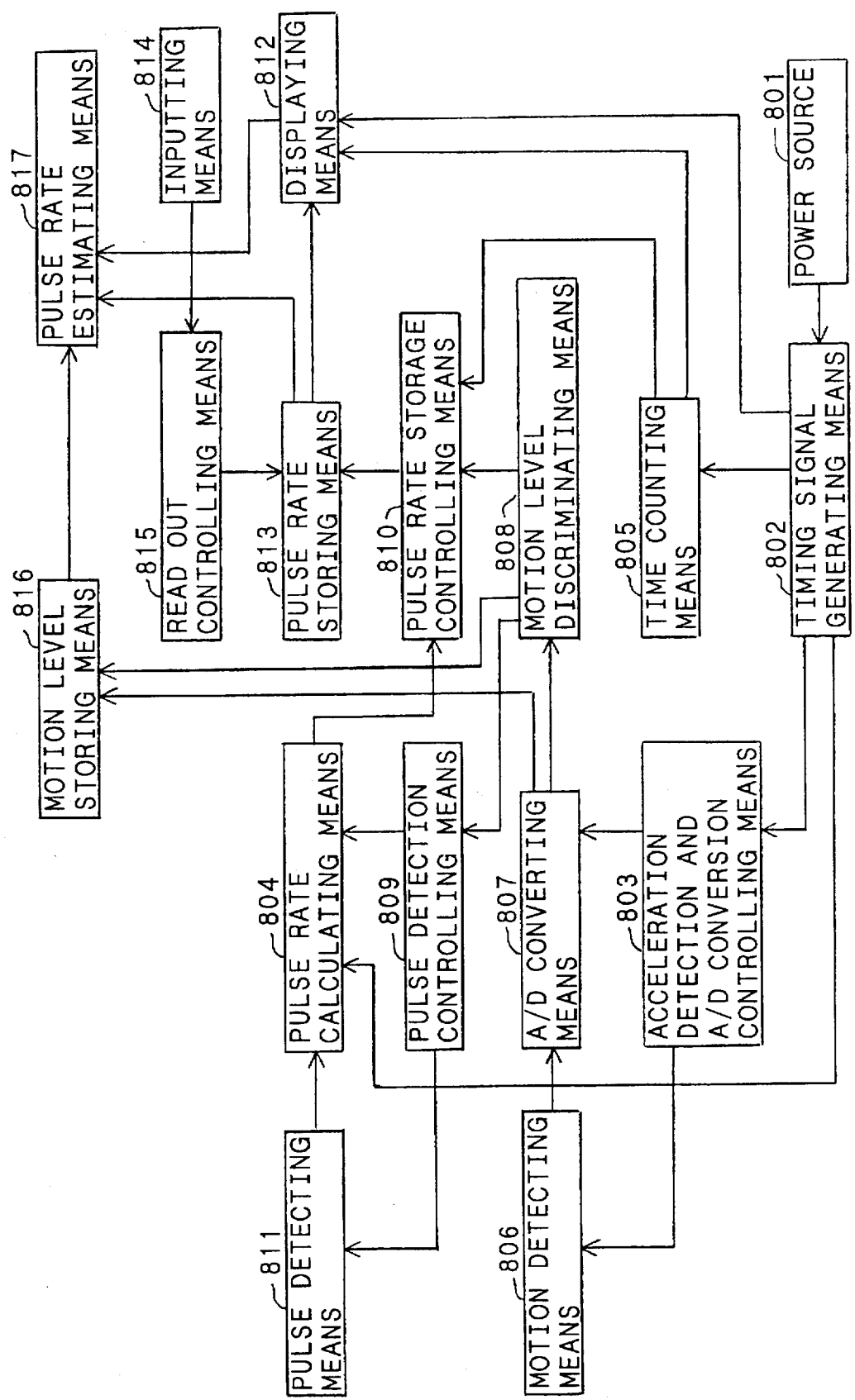
FIG. 8 is a functional block diagram showing other example of the structure of the present invention.

FIG. 8 is a block diagram wherein functions of storing a motion level when it exceeds a predetermined range, thus disallowing a pulse to be measured, and of estimating pulse rate data in the period during which no pulse could be measured from the stored motion level data and partially obtained pulse rate data are provided to the basic structure of the present invention shown in FIG. 1, beside the functions of activating the motion detection intermittently at predetermined intervals and of counting the current time. It allows a pulse rate transition pattern during a relatively heavy exercise such as jogging for example to be estimated from the motion level data and data related to exercise such as consumed calories to be estimated from the estimated pulse data transition pattern and the motion level data.

Again in FIG. 8, those functional blocks having the same function with those shown in FIG. 2 are designated with the same block number, with respect to their two lower digits, and explanation thereof will be partly omitted. Here, functional blocks added anew in FIG. 8 will be mainly explained.

Motion level storing means 816 stores an output signal of A/D converting means 807 during a period for which motion level discriminating means 808 has discriminated to be impossible to detect a pulse. Pulse rate estimating means 817 estimates a pulse rate transition pattern in the period during which no pulse could be measured from a pulse rate taken just before it became unmeasurable and a pulse rate taken after starting to measure a pulse input from pulse rate storing means 813 and from motion level data stored in motion level storing means 816 and outputs the estimated pulse rate to displaying means 812.

This embodiment allows the pulse rate transition pattern during exercise in which no pulse can be measured to be estimated. It then becomes possible to calculate calories expanded during exercise by using the estimated pulse rate.

Then, some concrete embodiments of the present invention will be explained below based on the drawings.

Figure 6:
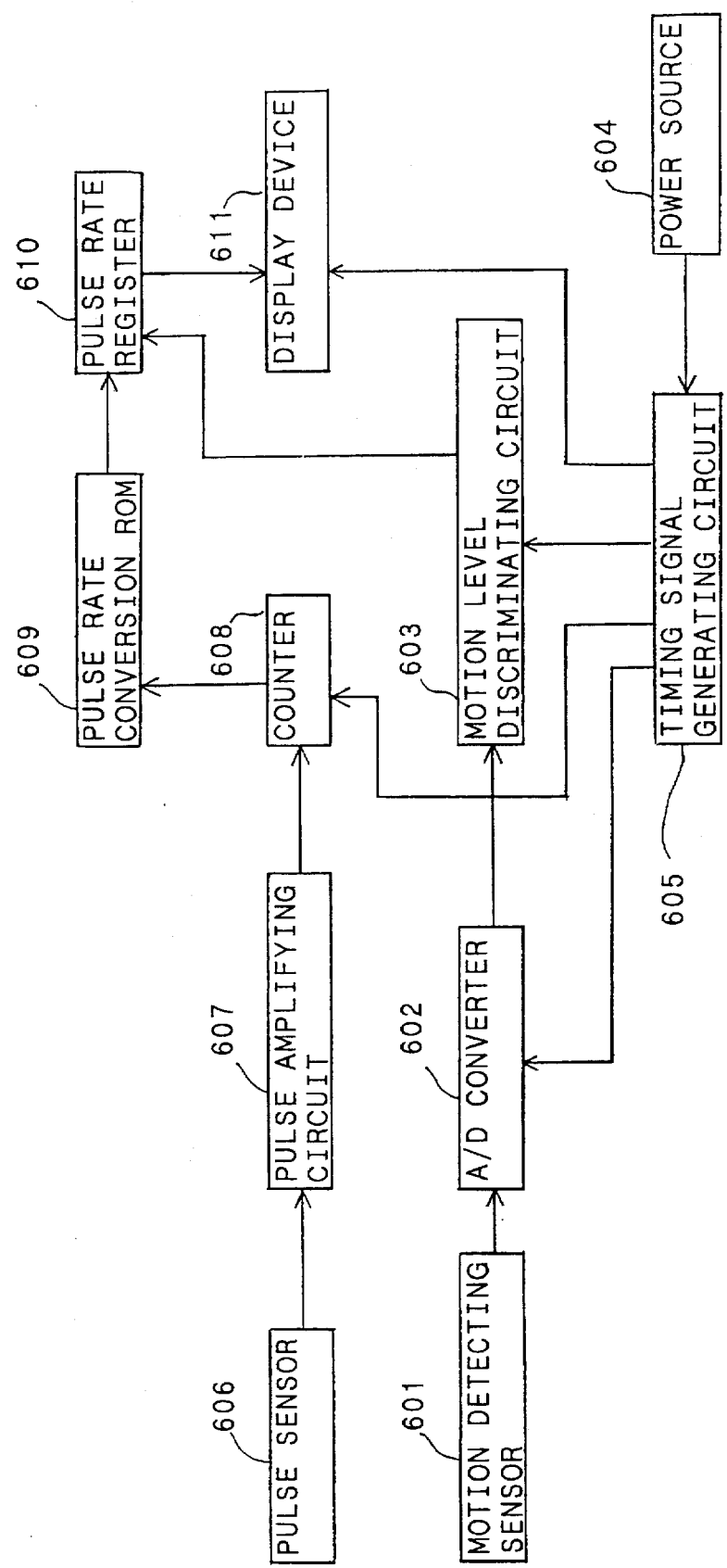
FIG. 6 is a system block diagram showing a first concrete embodiment of the present invention.

(1) First Concrete Embodiment:

FIG. 6 is a system block diagram showing a first concrete embodiment of a pulse rate monitor of the present invention. A timing signal generating circuit 605 which is operated by a power source 604 outputs a predetermined timing signal to an A/D converter 602, a counter 608, a motion level discriminating circuit 603 and a display device 611. A motion detecting sensor 601 outputs an analog voltage signal proportional to a motion of arms to the A/D converter 602.

The A/D converter 602 converts the analog voltage signal proportional to the motion of the arms output from the motion detecting sensor 601 into a digital signal by the timing signal from the timing signal generating circuit 605 and outputs it to the motion level discriminating circuit 603. When the level of the digital signal output from the A/D converter 602 is within a predetermined range, the motion level discriminating circuit 603 outputs a hold signal to a pulse rate register 610 based on the timing signal supplied from the timing signal generating circuit 605.

A pulse sensor 606 detects a pulse from a body and outputs the pulse signal to a pulse amplifying circuit 607. The pulse amplifying circuit 607 amplifies a small voltage signal input from the pulse sensor 606, shapes it into a rectangular pulse signal and outputs it to a counter 608. The counter 608 counts one period of the periodic signal of the pulse input from the pulse amplifying circuit 607 based on the clock signal inputted from the timing signal generating circuit 605 and outputs a result of the count to pulse rate conversion ROM 609.

For example, when the clock signal of the counter is 256 Hz and the period of the pulse signal output from the pulse amplifying circuit 607 is 1 Hz, a count of the counter 608 is then 256. The pulse rate conversion ROM 609 converts the counted value of the counter 608 into a pulse rate per minute and outputs it to the register 610. In the above case, the pulse rate conversion ROM 609 outputs 60 with 8 bit data.

The pulse rate register 610 holds the output of the pulse rate conversion ROM 609 by a hold signal from the motion level discriminating circuit 603 and outputs it to a display device 611. This hold signal is output from the motion level discriminating circuit 603 only when the motion of the arms is relatively mild and the pulse can be detected reliably. Accordingly, the latest pulse data at the time when a pulse can be measured reliably is always held in the pulse rate register 610. The display device 611 displays the data held in the pulse rate register 610 based on the timing signal from the timing signal generating circuit 605.

Figure 9:
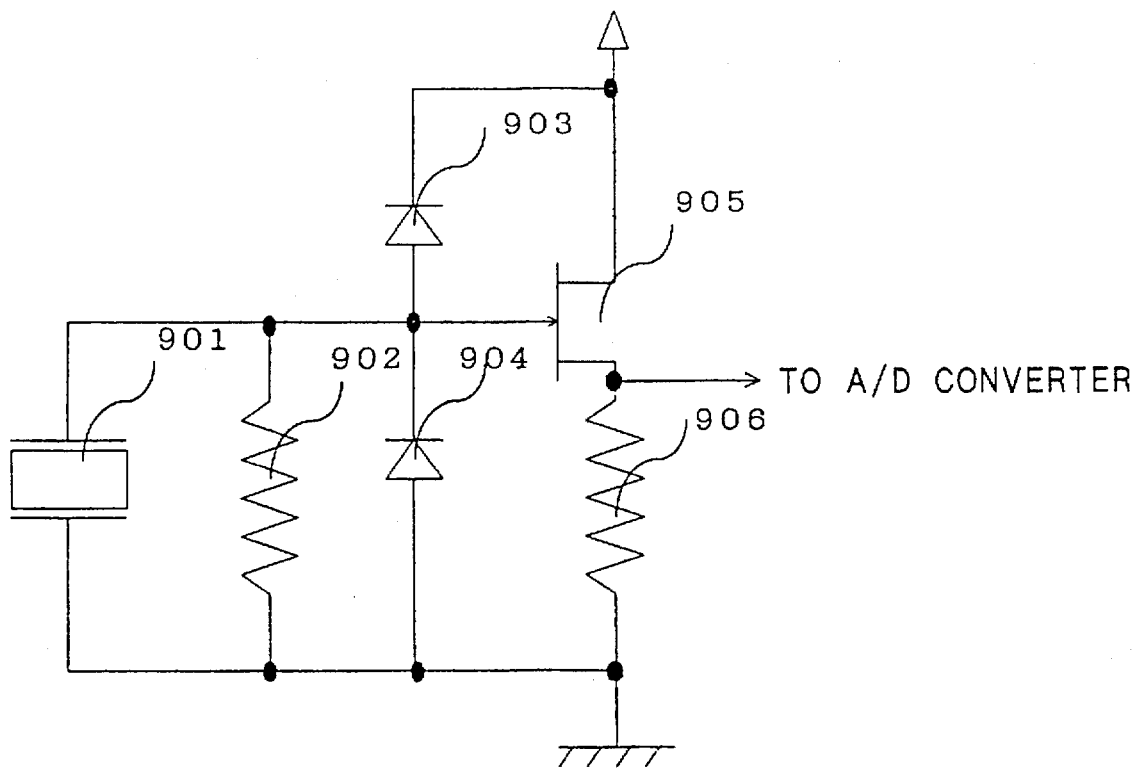
FIG. 9 is a diagram showing an example of a circuit of a motion sensor.

FIG. 9 shows a concrete example of the circuit of the motion detecting sensor. An acceleration sensor 901 generates a voltage proportional to a motion, e.g., the motion of the arms. A resistor 902 connected in parallel with the acceleration sensor 901 converts a charge generated by the acceleration sensor 901 due to an acceleration into a voltage. A diode 903 connected between the resistor 902 and a positive power source is a protective diode for releasing an over-voltage caused by a drop shock or the like to the positive power source. Similarly, a diode 904 connected in parallel with the resistor 902 is also a protective diode.

An FET 905 whose gate electrode is connected with an anode of the diode 903 and a cathode of the diode 904 reduces an output impedance of the acceleration sensor 901 together with a resistor 906 connected with a drain electrode thereof. The drain electrode of the FET 905 presents an output of the motion detecting sensor. While the first concrete embodiment has been explained in a mode in which the drain electrode of this FET 905 is connected directly with the A/D converter, it may become necessary to provide an amplifying circuit such as an operational amplifier depending on the level of this output voltage. Because such amplifying circuit may be readily realized, its explanation has been omitted.

Figure 10:
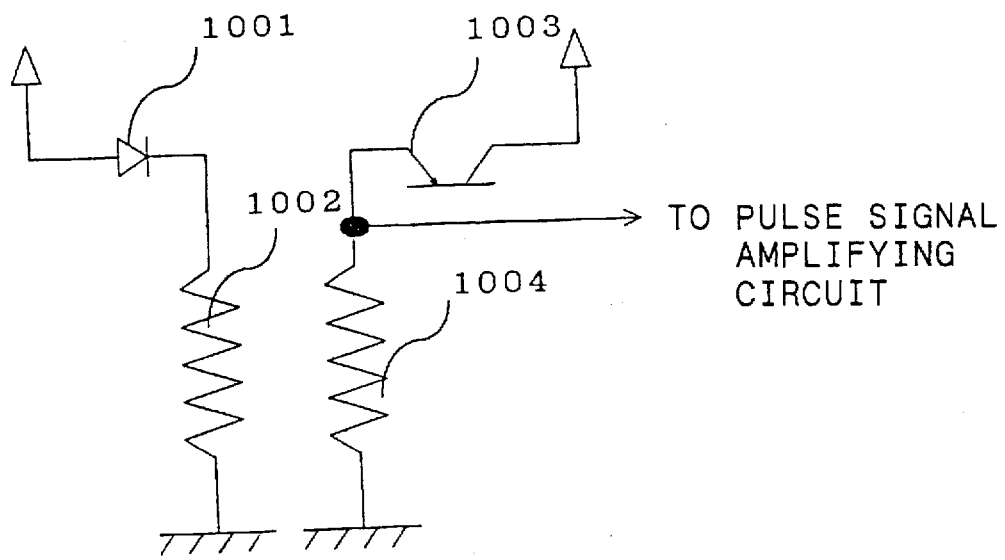
FIG. 10 is a diagram showing an example of a circuit of a pulse sensor.

FIG. 10 shows a concrete example of the pulse sensor. An LED 1001 whose anode electrode is connected with a positive power source emits light by a current supplied via a current restricting resistor 1002 connected with a cathode thereof. A phototransistor 1003 whose collector electrode is connected with a positive power source generates a photoelectric current by receiving a reflected light from the body to which the LED 1001 has illuminated and flows the current to a resistor 1004 connected to an emitter thereof. A voltage generated in the resistor 1004 due to that current becomes an output of the pulse sensor.

According to the pulse rate monitor constructed as described above, only reliable pulse data may be held by always monitoring the motion level and incorrect pulse data affected by the motion level may be eliminated. Due to that, the user can obtain the pulse data continuously at predetermined time intervals without being conscious about the measuring environment.

Figure 11:
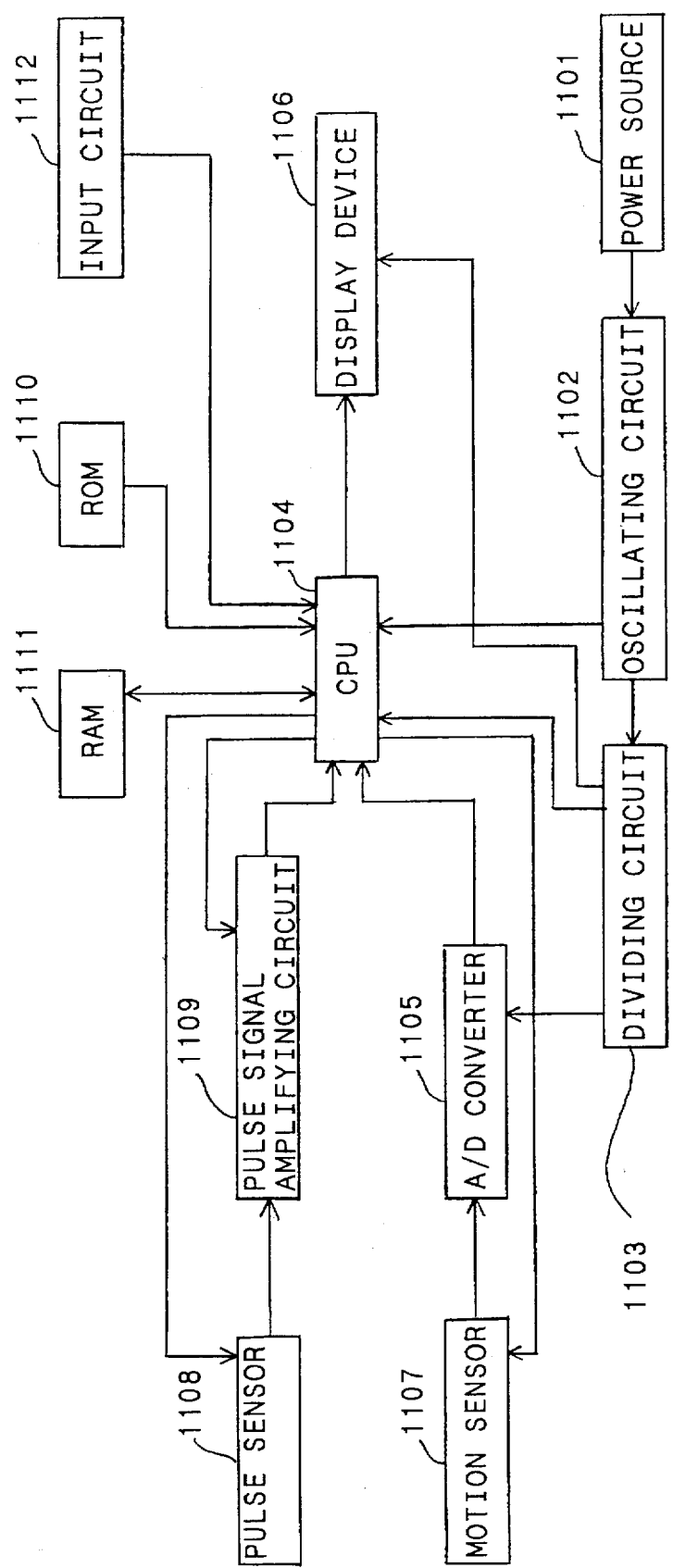
FIG. 11 is a system block diagram showing a second concrete embodiment of the present invention.

(2) Second Concrete Embodiment:

FIG. 11 is a system block diagram showing a second concrete embodiment of the pulse rate monitor of the present invention. FIG. 11 shows an embodiment realizing the present invention by one-chip microcomputer comprising a CPU, a ROM and a RAM.

An oscillating circuit 1102 operated by a power source 1101 outputs its oscillatory output to a dividing circuit 1103 as a reference signal for counting time and to the CPU 1104 as a system clock for operation. The dividing circuit 1103 divides the oscillatory signal input from the oscillating circuit 1102 and outputs a required frequency signal to an A/D converter 1105, the CPU 1104 and a display device 1106.

A motion sensor 1107 outputs an analog voltage signal proportional to a motion of the user's arms to the A/D converter 1105 based on an operation enable signal from the CPU 1104. The A/D converter 1105 converts the analog voltage signal output from the motion sensor 1107 into a digital signal and outputs it to the CPU 1104.

A pulse sensor 1108 detects a pulse signal of the body based on the operation enable signal from the CPU 1104 and outputs the pulse signal to a pulse signal amplifying circuit 1109. Based on the operation enable signal from the CPU 1104, the pulse signal amplifying circuit 1109 amplifies the small pulse voltage signal input from the pulse sensor 1108, shapes its waveform and outputs a periodic signal of the pulse to the CPU 1104. The CPU 1104 carries out the following process in accordance to a processing step programmed in the ROM 1110.

First, it carries out a process of counting the current time by counting the reference frequency signal for counting time from the dividing circuit 1103. At this time, part of the RAM 1111 is used as a register for counting time.

Second, it activates the motion sensor 1107 periodically by counting the reference frequency signal from the dividing circuit 1103, reads the digital signal from the A/D converter 1105 and based on the level of the digital signal at that time, discriminates whether it is possible to detect a pulse.

Third, when it is possible to detect a pulse, it activates the pulse sensor 1108 and the pulse signal amplifying circuit 1109 to count the period of the pulse output from the pulse signal amplifying circuit 1109 and converts the period into a pulse rate per minute.

Fourth, it stores the data converted into the pulse rate to the RAM 1111 and outputs the pulse data to the display device 1106.

A result of such processing by the CPU is displayed on the display device 1106. Further, it is possible to read pulse rate data and time data in any address in the RAM 1111 and to display them on the display device 1106 by a control signal input to the CPU 1104 from an input circuit 1112.

Figure 12:
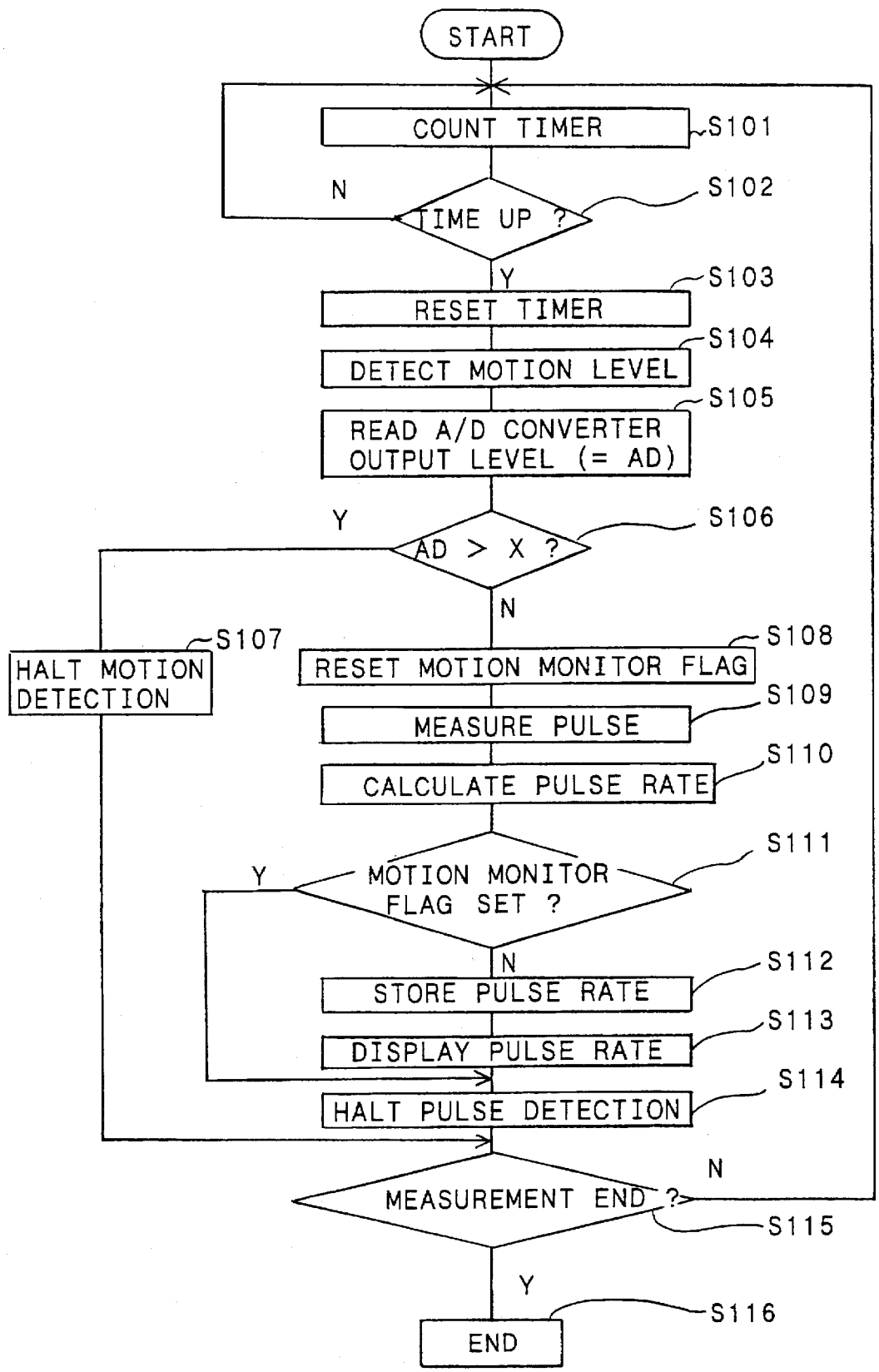
FIG. 12 is a chart showing a flow of an operation in measuring a pulse.

FIG. 12 shows a flow of the operation in measuring a pulse and it will be explained in detail in conjunction with FIG. 11.

When a pulse measuring state is started (START), the CPU counts 1 Hz interruption for example from the dividing circuit 1103 by 60 times in "COUNT TIMER" (S101). When it confirms the count of 60 times in "TIME UP?" (S102), it resets the timer in "RESET TIMER" (S103) and then starts the operation of the motion sensor 1107 in "DETECT MOTION LEVEL" (S104).

After starting the motion sensor 1107, it reads the output signal of the A/D converter 1105 in "READ A/D CONVERTER OUTPUT LEVEL" (S105). It then discriminates whether the read data AD exceeds a pulse detectable level X or not in "AD>X?" (S106). When the data AD is greater than the pulse detectable level X, i.e., when it is determined that it is impossible to detect a pulse, it halts the operation of the motion sensor 1107 in "HALT MOTION DETECTION" (S107). After halting the operation of the motion sensor 1107, it confirms whether the pulse measuring state has been finished or not in "MEASUREMENT END?" (S115) and when it has been finished, it ends the pulse measuring state in "END" (S116). When the pulse measuring state continues, it returns again to "COUNT TIMER" (S101) to count the timer to be ready for the next measurement.

When the read data AD is smaller than the pulse detectable level X in "AD>X?" (S106), i.e., when it is discriminated that it is possible to measure a pulse, the CPU resets a motion monitor flag existing within the RAM 1111, to be set when the read data AD exceeds X for the purpose of monitoring the motion during the measurement, in "RESET MOTION MONITOR FLAG" (S108). After resetting the motion monitor flag, it starts the operation of the pulse sensor 1108 and the pulse signal amplifying circuit 1109 to start the measurement of pulse in "MEASURE PULSE" (S109). After starting the measurement, the CPU 1104 carries out a calculation of pulse rate for converting the periodic signal of the pulse input to the CPU 1104 into a pulse rate per minute in "CALCULATE PULSE RATE" (S110). After finding the pulse rate in "CALCULATE PULSE RATE" (S110), it confirms whether a heavy motion which would disable the measurement has been made or not during the measurement in "MOTION MONITOR FLAG SET?" (S111).

Although not shown in the flow chart in FIG. 12, the data AD of the A/D converter 1105 is read periodically to monitor whether it exceeds the pulse detectable level X or not and when it exceeds level X, a process for setting the motion monitor flag in the RAM 1111 is carried out. When it is confirmed in "MOTION MONITOR FLAG SET?" (S111) that the flag has been set, the operation of the pulse detecting circuit is halted in "HALT PULSE DETECTION" (S114) and the obtained pulse data is discarded.

Then, it discriminates whether the pulse measuring state is continuing or not in "MEASUREMENT END?" (S115) and when the measurement has been finished, it ends the measurement in "END" (S116), and when it is continued, it returns to "COUNT TIMER" (S101) to be ready for the next measurement.

After confirming in "MOTION MONITOR FLAG SET?" (S111) that the motion monitor flag is not set during the measurement of pulse, it stores the obtained pulse rate data in the RAM 1111 in "STORE PULSE RATE" (S112). After storing the data, it displays the pulse rate data on the display device 1106 in "DISPLAY PULSE RATE" (S113). At this time, it can display the time when the pulse rate data has been obtained together with the pulse rate.

After displaying the pulse rate data, it halts the operation of the pulse sensor 1108 and the pulse signal amplifying circuit 1109 in "HALT PULSE DETECTION" (S114). After executing "HALT PULSE DETECTION" (S114), it returns to "COUNT TIMER" (101) again to be ready for the next measurement when the pulse measuring state is continuing. When the pulse measuring state has finished, it ends the pulse measuring state in "END" (S116).

While the basic operation of the present invention in measuring a pulse has been described, an arrangement for providing even more useful data to the user may be realized by using the pulse data measured through this basic operation.

For example, it is possible to determine health and mental conditions from the comparison of the reference transition pattern of the standard pulse and the actually measured transition pattern of the measured pulse. In the case of the system block diagram of FIG. 11, the standard stored pulse data may be compared with the actually measured data even if it is stored in the RAM 1111 or the ROM 1110. Non-user specific general reference transition patterns are stored in the ROM 1110 as fixed data. A reference transition pattern which matches with characteristics of the individual user may be written and stored in the RAM 1111 as necessary and may be readily rewritten.

In either of these cases, it becomes possible to evaluate the health condition and the mental stability of the user by programming a process in the ROM 1110 for comparing the stored data with the actually measured data and for determining the user's physical or mental state from the comparison results, accounting for a certain range. The data to be compared with actually measured data may include a reference transition pattern of a pulse rate taken during a light exercise which will not disable the measurement of a pulse, a reference transition pattern of a pulse rate taken during sleeping or a reference transition pattern of a pulse rate taken in a rest state. By comparing with these reference transition patterns, it becomes possible to discriminate and evaluate data related to a quality of sleeping such as a frequency and duration time of so called paradox sleeping (REM sleeping) for example. Further, by storing the reference transition pattern of the pulse rate in the quiet state, it becomes possible to determine and evaluate the mental stability from the fluctuation of the actually measured pulse rate transition pattern.

As another concrete use example, there is an arrangement of estimating a transition of pulse rate during an unmeasurable time from a pulse rate measured just before it becomes impossible to measure the pulse, a pulse rate after restarting to measure a pulse and motion level data during the unmeasurable period. Such arrangement may be realized by adequately changing the program in the ROM 1110 in the case of the system block diagram in FIG. 11.

Figure 13:
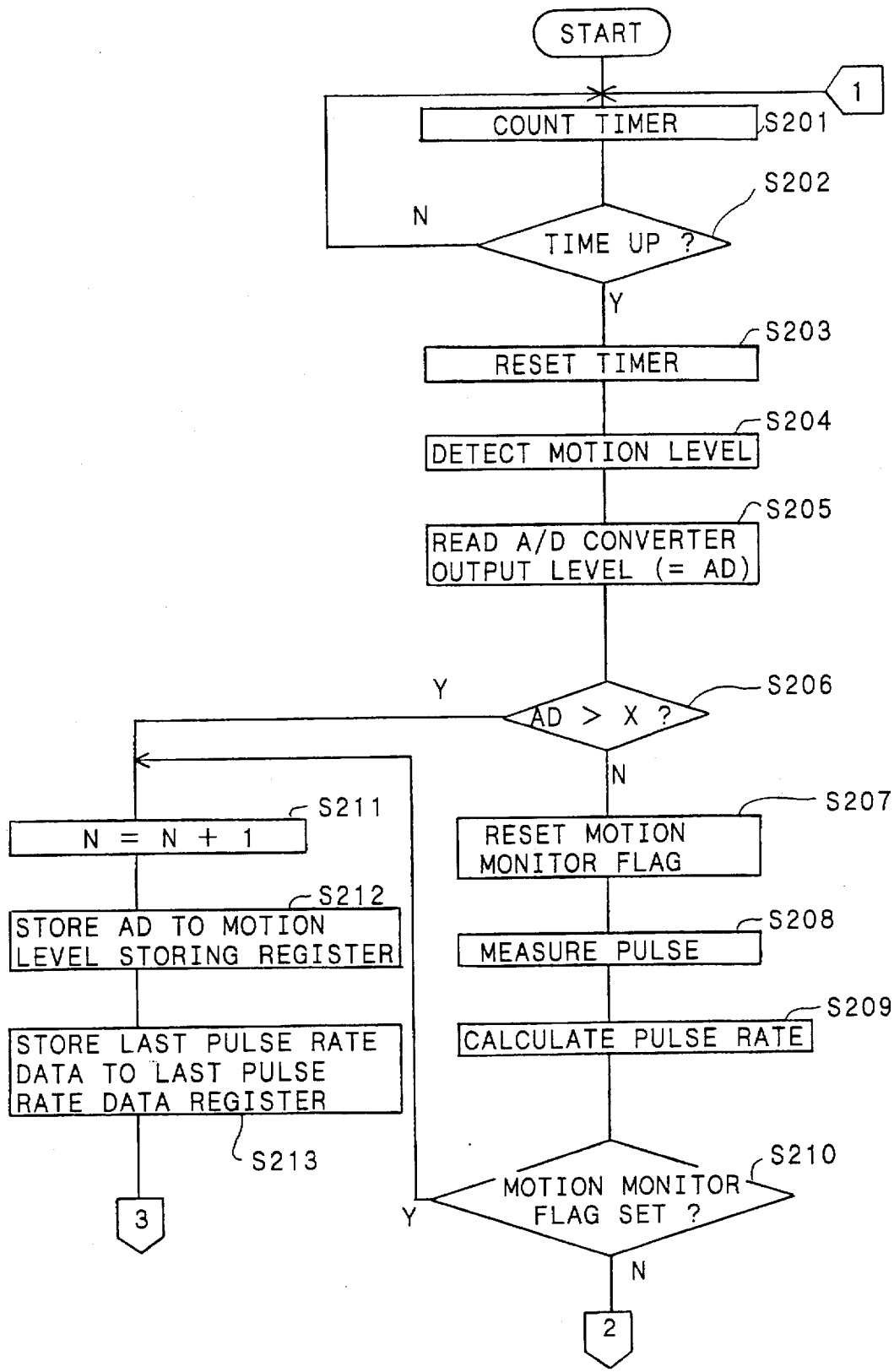
FIG. 13 is a chart showing one part of another flow of an operation in measuring a pulse.

The operation of the process for estimating the pulse transition during such unmeasurable time shown in FIGS. 13 and 14 will be explained below in conjunction with FIG. 11. Among the flow of the operation in measuring pulse in FIGS. 13 and 14, the same processing steps with those in the flow of the operation described in FIG. 12 will be designated with the same Step number, with respect to two lower digits, and an explanation thereof will be partially omitted here.

The output signal of the A/D converter 1105 is read in "READ A/D CONVERTER OUTPUT LEVEL" (S205) to discriminate whether the read data AD exceeds the pulse detectable level or not in "AD>X?" (S206). When the data AD is greater than the pulse detectable level X, an unmeasurable counter N is counted up for the purpose of monitoring a time during which no pulse has been able to be measured continuously for more than a certain period (S211). After counting up, an output level of the A/D converter at that time, e.g., a signal proportional to the swinging of the user's arms, is stored in a motion level storing register provided within the RAM 1111 (S212).

After storing the output of the A/D converter, the last data of the pulse rate data stored in the RAM 1111 successively in a time-series manner is read and is stored in a last pulse rate data register provided within the same RAM 1111 (S213). After storing in the last pulse rate data register, the operation of the motion sensor 1107 is halted in "HALT MOTION DETECTION" (S223). After halting the operation of the motion sensor 1107, it is confirmed whether the pulse measuring state has been finished or not in "MEASUREMENT END" (S224), and it has been finished, the pulse measuring state is ended in "END" (S225). When the pulse measuring state is continuing, the process returns to "COUNT TIMER" (S201) to be ready for the next measurement and waits for the next time up.

When the data AD is large and no pulse can be measured as such, the motion at that time, e.g., the digital signal proportional to the swinging of the user's arms for example, is stored continuously in the motion level storing register provided within the RAM 1111 and its period is equal to a timer count time. Accordingly, by seeing the data of the motion level storing register, it is possible to know an intensity and continuing time of exercise, supposing that a quantity of motion is great when the arms are swung strongly.

Next, an operation carried out when it is possible to detect a pulse will be explained. When the read data AD is smaller than the pulse detectable level X in "AD>X?" (S206), the motion monitor flag within the RAM 1111 is reset for the purpose of monitoring the motion during the measurement (S207). After resetting the motion monitor flag, the CPU 1104 starts the operation of the pulse sensor 1108 and the pulse signal amplifying circuit 1109 to start the measurement. After starting the measurement, it carries out a calculation of pulse rate for converting the periodic signal of the pulse input to the CPU 1104 into a pulse rate per minute in "CALCULATE PULSE RATE" (S209).

After finding the pulse rate, it checks by the motion monitor flag whether a heavy motion that would have disabled the measurement has been made or not during the measurement of the pulse rate now obtained (S210). When such heavy motion that would have disabled the measurement has been made during the measurement, it discards the obtained pulse rate data, jumps to a process of counting up the unmeasurable counter N (S211) which is a process in the pulse unmeasurable state, to execute that process and thereafter and waits for the next time up.

When no motion that would have disabled the measurement has been made during the measurement, the CPU stores the obtained pulse rate data in the RAM 1111 (S214). After storing data in the RAM 1111, it stores the measured data in the latest pulse rate data register provided within the RAM 1111 too. After storing in the latest pulse rate data register, it displays the pulse rate data on the display device 1106 (S216). After displaying it, it checks the value N of the unmeasurable counter to confirm whether the unmeasurable state has continued for more than a predetermined period before the pulse rate data just obtained (S217). In this flow-chart, the count time which corresponds to the predetermined period is set at 10 and the timer time is set at one minute, so that it is checked whether the unmeasurable state has lasted for 10 minutes. When the count value N of the unmeasurable counter is less than 10, the unmeasurable counter is reset to zero (S221).

When the count value N of the unmeasurable counter is equal to or greater than 10, a transition of pulse rate during the unmeasurable period is estimated by calculating from the latest pulse rate data stored in the latest pulse rate data register, the last pulse rate data in the last pulse rate data register which stores the pulse rate taken before it became unmeasurable successively and the data in the motion level data register which stores the motion level data during the unmeasurable period (S218). When it is estimated by calculation, it becomes possible to make an estimation in which characteristics of each individual is taken into account by preparing not only a uniform estimation but also parameters which shows features of individual differences within the RAM 1111. The estimated data is stored in a storage domain provided within the RAM 1111 (S219). After storing it, the unmeasurable counter is reset to zero (S220).

After resetting the unmeasurable counter, it halts the operation of the pulse detecting circuit composed of the pulse sensor and the pulse signal amplifying circuit 1109 (S222). After halting the operation of the pulse detecting circuit, it confirms whether the pulse measuring state has finished or not in "MEASUREMENT END?" (S224), and when it has finished, it ends the pulse measuring state in "END" (S225). When the measuring state continues, it returns to "COUNT TIMER" (S201) to wait for the next time up.

As described above, it estimates by calculating the pulse rate transition only when the count value N of the unmeasurable counter is equal to or greater than 10. It is because that it is considered to be meaningless to estimate a short term pulse transition. The time during which the transition is estimated may be readily changed by changing the count value N of the unmeasurable counter.

Thus, the function of estimating the pulse transition during the unmeasurable period allows consumed calories during exercise to be calculated from the estimated pulse rate transition pattern. Further, it allows an intensity of exercise of the user to be estimated from the estimated value of the maximum pulse rate.

Figure 15A:
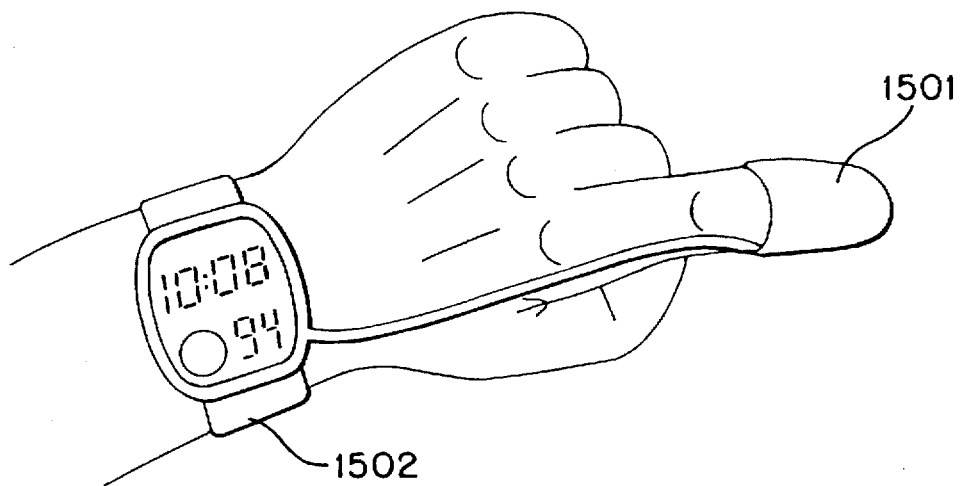
FIGS. 15A and 15B are drawings showing outside views of the inventive pulse rate monitor.
Figure 15B:
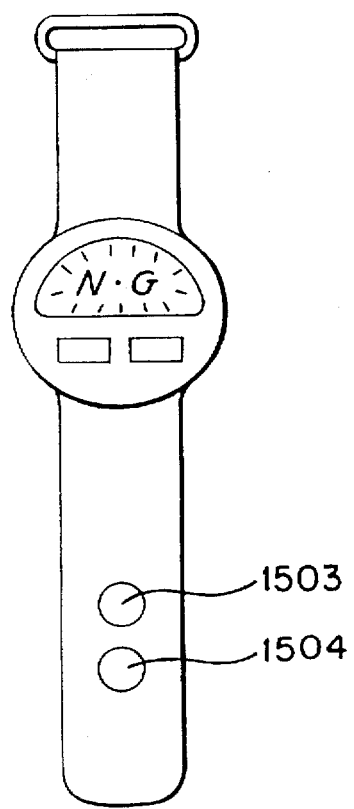

FIG. 15 shows outside views of the inventive pulse rate monitor. Two kinds of outside views are shown due to a difference of parts where the sensor is mounted. FIG. 15A shows a case when a finger-suck type sensor 1501 is used, wherein an output signal of the sensor is connected to a watch head 1502 with a cable. FIG. 15B is an outside view when sensors 1503 and 1504 of piezoelectric microphone type are disposed at the radius portion of the wrist.

What is claimed is:

1. A pulse rate monitor, comprising: motion detecting means for detecting motion of a user using a motion sensor and for outputting an analog signal having a characteristic that varies in accordance with the magnitude of detected motion; A/D converting means for converting the output analog signal of the motion detecting means into a digital signal; motion level discriminating means for discriminating whether it is possible to accurately measure the user's pulse based on the digital signal output from the A/D converting means and for outputting a control signal when a result of the discrimination indicates that accurate pulse measurement is possible; pulse detecting means for detecting the user's pulse and outputting a periodic signal corresponding to the detected pulse; pulse rate calculating means for converting the periodic signal output from the pulse detecting means into pulse rate data; pulse rate storing means for storing the pulse rate data output from the pulse rate calculating means in response to the control signal output from the motion level discriminating means; display means for displaying the pulse rate data output from the pulse rate storing means; and timing signal generating means for outputting a predetermined timing signal to the pulse rate calculating means and the display means.

2. A pulse rate monitor according to claim 1; further comprising time counting means for counting the current time; pulse detection controlling means for controlling the activation and deactivation of the pulse detecting means and the pulse rate calculating means depending upon the control signal output from the motion level discriminating means; pulse rate storage controlling means for controlling the pulse rate storing means to store the pulse rate data output from the pulse rate calculating means and the time data of the time counting means when the output of the pulse detection controlling means permits pulse detection; read out controlling means for providing an address used for reading out contents stored in the pulse rate storing means; inputting means for controlling the read out controlling means at an arbitrary timing; acceleration detection and A/D conversion controlling means for activating the motion detecting means and the A/D converting means intermittently at predetermined intervals; wherein the display means includes means for displaying the time data of the time counting means and the timing signal generating means includes means for outputting the predetermined timing signal to the acceleration detection and A/D conversion controlling means and the time counting means.

3. A pulse rate monitor according to claim 2; further comprising pattern storing means for storing a reference transition pattern of a predetermined pulse rate; pattern comparing means for comparing a transition pattern of a measured pulse rate stored in the pulse rate storing means with the reference transition pattern stored in the pattern storing means; and comparison result discriminating means for discriminating characteristics of the actually measured pulse rate transition pattern in accordance with a result of comparison performed by the pattern comparing means.

4. A pulse rate monitor according to claim 2; further comprising motion level storing means for storing an output signal of the A/D converting means when an output of the motion level discriminating means indicates that it is impossible to accurately measure a pulse; and pulse rate estimating means for estimating pulse rate data during the time that an accurate pulse rate cannot be measured based on the motion level data stored in the motion level storing means and the pulse rate data stored in the pulse rate storing means.

5. A pulse rate monitor comprising: time counting means for counting the current time and producing time data; motion detecting means for detecting motion using a motion sensor and outputting a corresponding analog signal; A/D converting means for converting the analog signal of the motion detecting means into a digital signal; motion level discriminating means for discriminating whether it is possible to accurately measure a pulse based on the digital signal output from the A/D converting means and for outputting a control signal corresponding to a result of the discrimination; pulse detecting means for detecting a pulse from a living body and outputting a periodic signal corresponding to the detected pulse; pulse rate calculating means for converting the periodic signal corresponding to the detected pulse output from the pulse detecting means into pulse rate data; pulse detection controlling means for controlling the activation and deactivation of the pulse detecting means and the pulse data calculating means based on the control signal from the motion level discriminating means; pulse rate storing means for storing pulse rate data output from the pulse rate calculating means and for storing corresponding time data of the time counting means; pulse rate storage controlling means for controlling the pulse rate storing means to store the pulse rate data and the time data based on an output of the pulse detection controlling means; read out controlling means for providing an address for reading out contents stored in the pulse rate storing means; inputting means for controlling the read out controlling means with an arbitrary timing; display means for displaying the data of the pulse rate storing means; and timing signal generating means for outputting a predetermined timing signal to the pulse rate calculating means, the time counting means and the display means.

6. A pulse rate monitor according to claim 5; further comprising motion detection and A/D conversion controlling means for activating the motion detecting means and the A/D converting means intermittently at predetermined intervals.

7. A pulse rate monitor according to claim 5; further comprising pattern storing means for storing a reference transition pattern of a predetermined pulse rate; pattern comparing means for comparing a transition pattern of a measured pulse rate stored in the pulse rate storing means with the reference transition pattern stored in the pattern storing means; and comparison result discriminating means for discriminating characteristics of the measured pulse rate transition pattern in accordance with a result of the comparison performed by the pattern comparing means.

8. A pulse rate monitor according to claim 5; further comprising motion level storing means for storing an output signal of the A/D converting means when an output of the motion level discriminating means indicates that it is not possible to accurately measure a pulse; and pulse rate estimating means for estimating pulse rate data during the time that an accurate pulse cannot be measured based on the motion level data stored in the motion level storing means and the pulse rate data stored in the pulse rate storing means.

9. A pulse rate monitor for determining the pulse rate of a user, comprising: motion detecting means for detecting motion of the user and outputting a movement signal having a characteristic that varies in accordance with the magnitude of the movement; motion level discriminating means for determining whether it is possible to accurately measure the user's pulse based upon the magnitude of the detected movement; pulse rate measurement means for detecting the user's pulse and calculating the user's pulse rate; and display means for displaying the calculated pulse rate.

10. A pulse rate monitor according to claim 9; wherein the motion detecting means comprises an acceleration sensor and the motion level discriminating means comprises an A/D converter for converting an analog signal output by the motion sensor into a digital signal and a microprocessor for analyzing the digital signal and determining whether an accurate pulse measurement can be taken based upon the magnitude of the detected movement.

11. A pulse rate monitor according to claim 9; wherein the pulse rate measurement means comprises means using a light emitting diode for projecting a light into the user's body and a phototransistor for detecting light reflected from the user's body and producing a pulse signal in accordance with the detected light, and a microprocessor for calculating the user's pulse rate based upon the time difference between successively detected pulse signals.

12. A pulse rate monitor according to claim 9; further comprising a memory for storing a pulse rate value measured when the motion level discriminating means has determined that the user's pulse can accurately be measured.

13. A pulse rate monitor according to claim 9; further comprising means for counting time; and means for controlling the motion detecting means to intermittently detect motion of the user at predetermined intervals to reduce power consumption of the pulse rate monitor.

14. A pulse rate monitor according to claim 9; further comprising means for deactivating the pulse rate measurement means when the motion level discriminating means has determined that the user's pulse cannot be accurately measured.

15. A pulse rate monitor according to claim 9; further comprising pattern storing means for storing a reference transition pattern of a predetermined pulse rate; pattern comparing means for comparing a measured transition pattern of a pulse rate stored in the memory with the reference transition pattern stored in the pattern storing means; and means for determining the characteristics of the measured pulse rate transition pattern based upon a result of the comparison.

16. A pulse rate monitor according to claim 9; further comprising a memory for storing a most recent pulse rate value measured during a period when the motion level discriminating means has determined that the user's pulse can be accurately measured; storing means for storing the movement signal; and pulse rate estimating means for estimating the user's pulse rate during periods of time when the motion level discriminating means determines that the user's pulse cannot be accurately measured based upon the movement signal and the most recent pulse rate value stored in the memory.

17. A pulse rate monitor comprising: motion detecting means for detection motion of a user using a motion sensor and for outputting an analog signal having a characteristic that varies in accordance with the magnitude of detected motion; A/D converting means for converting the output analog signal of the motion detecting means into a digital signal; motion level discriminating means for discriminating whether it is possible to accurately measure the user's pulse based on the digital signal output by the A/D converting means and for outputting a control signal when a result of the discrimination indicates that accurate pulse measurement is possible; pulse detecting means for detecting the user's pulse and outputting a periodic signal corresponding to the detected pulse; pulse rate storing means for storing the pulse rate data output by the pulse rate calculating means in response to the control signal output by the motion level discriminating mean; display means for displaying the pulse rate data output from the pulse rate storing means; time counting means for counting current time and producing time data; pulse detection controlling means for controlling the activation and deactivation of the pulse detecting means and the pulse rate calculating means depending upon the control signal output by the motion level discriminating means; pulse rate storage controlling means for controlling the pulse rate storing means to store the pulse rate data output by the pulse rate calculating means and the time data of the time counting means when the output of the pulse detection controlling means permits pulse detection; read out controlling means for providing an address used for reading out contents stored in the pulse rate storing means; input means for controlling the read out controlling means at an arbitrary timing; acceleration detection and A/D conversion controlling means for activating the motion detecting means and the A/D converting means intermittently at predetermined intervals; display means for displaying the pulse rate data stored in the pulse rate storing means and the time data of the time counting means; and timing signal generating means for outputting a predetermined timing signal to the pulse rate calculating means, the time counting means, the display means and the acceleration detection and A/D conversion controlling means.

* * * * *